United States Patent [19]
Joo et al.

[11] Patent Number: 5,770,774
[45] Date of Patent: *Jun. 23, 1998

[54] METHOD FOR PREPARING 2-METHYL-1,4-NAPHTHOQUINONE (VITAMIN K₃)

[75] Inventors: Young J. Joo; Jin-Eok Kim; Jeong-Im Won; Kum-Ui Hwang, all of Taejeon, Rep. of Korea

[73] Assignee: Korea Kumho Petrochemical Co., Ltd., Seoul, Rep. of Korea

[*] Notice: The term of this patent shall not extend beyond the expiration date of Pat. No. 5,723,675.

[21] Appl. No.: 758,921

[22] Filed: Dec. 2, 1996

[30] Foreign Application Priority Data

Apr. 25, 1996 [KR] Rep. of Korea ..................... 96-12872

[51] Int. Cl.⁶ ..................................................... C07C 46/00
[52] U.S. Cl. ............................................................ 568/317
[58] Field of Search ..................................... 568/317, 312, 568/328

[56] References Cited

PUBLICATIONS

Chem Rev 1993, 93, 741–761 Pindur "Acceleration & Selectivity Enhancement of Diels Alder Raction, et".
Liebigs Ann. Chem 1993 905–909 Khanbabaee "Total Synthesis of Hallachrome et al".
Sigma Chem Cataloge 1996 p. 688.

*Primary Examiner*—Gary Geist
*Assistant Examiner*—Jean F. Vollano
*Attorney, Agent, or Firm*—Harrison & Egbert

[57] ABSTRACT

A method for preparing 2-methyl-1,4-naphthoquinone (vitamin K₃), in which 2-methyl-1,4-benzoquinone and 1,3-butadienes are subjected to a [2+4] Diels-Alder reaction and subsequently to oxidative dehydrogenation, using dimethylsulfoxide as both a dehydrogenating agent and a solvent in the presence of at least one Lewis acid or a Broensted acid, in a single pot, shows high selectivity and yield.

5 Claims, No Drawings

METHOD FOR PREPARING 2-METHYL-1,4-NAPHTHOQUINONE (VITAMIN K₃)

BACKGROUND OF THE INVENTION

1. Field of the Invention

The present invention relates to a method for preparing 2-methyl-1,4-naphthoquinone (vitamin K$_3$) comprising being subjected to a [2+4] Diels-Alder reaction of 2-methyl-1,4-benzoquinone and 1,3-butadiene simultaneously while dehydrogenating them, so that the [2+4] Diels-Alder reaction and dehydrogenation are continuously performed and completed in a single pot.

When 2-methyl-1,4-benzoquinone as a dienophile for a [2+4] Diels-Alder reaction is reacted with 1,3-butadienes, 2-methyl-4a,5,8,8a-tetrahydro-1,4-naphthoquinone may be almost quantitatively obtained without generating by-products. The present invention relates to a method, in which by using an oxidant being capable of dehydrogenating without oxidizing double bonds, 2-methyl-4a,5,8,8a-tetrahydro-1,4-naphthoquinone produced through a [2+4] Diels-Alder reaction is converted into 2-methyl-1,4-naphthoquinone, without separation and purification, in one pot.

2. Description of the Prior Art

2-Methyl-1,4-naphthoquinone may be prepared from 2-methyl-1,4-benzoquinone and 1,3-butadiene through a [2+4] Diels-Alder reaction and dehydrogenation as shown in the following reaction scheme:

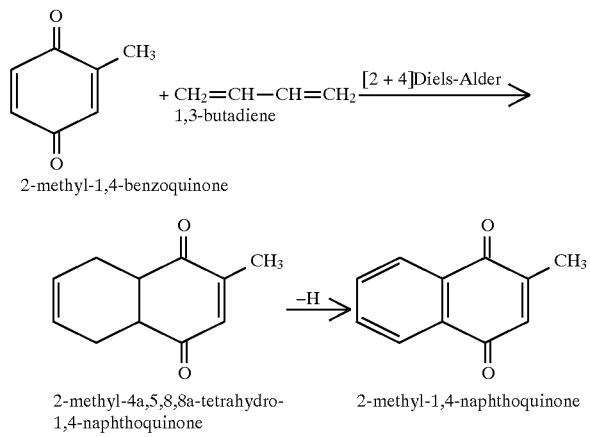

2-methyl-1,4-benzoquinone 2-methyl-4a,5,8,8a-tetrahydro-1,4-naphthoquinone 2-methyl-1,4-naphthoquinone 2-Methyl-1,4-naphthoquinone, also called "menadione" as a common name, is the most important compound of 1,4-naphthoquinones. It is the most simple vitamin K of vitamin Ks, a vitamin having a coagulation effect on blood. Also, 2-methyl-1,4-naphthoquinone is an important, fine chemical material, which is used as an intermediate for vitamin K$_1$, vitamin K$_2$ and dye. This is why intensive research has been made for its preparation method.

2-Methyl-1,4-naphthoquinone is generally prepared by oxidizing 2-methylnaphthalene. The preparing methods using the following oxidants are well known:

A. oxidation using chromic acid (J. Am. Chem. Soc. 61 (1939), p3216),

B. oxidation using hydrogen peroxide (Japanese Pat. Laid-Open Publication Nos. Sho. 52-108959 (1977), 53-50147 (1978) and 59-53252 (1984) and EP No. 247,513 (1987)), and C. liquid- or gas-phase oxidation, using barium oxide and copper halide (Japanese Pat. Laid-Open Nos. Sho. 61-221148 (1986), 64-90151 (1986), Hei. 6-9485 (1994) and 6-172254 (1994)).

Moreover, a method which comprises reacting ruthenium trichloride (RuCl$_3$) with ammonium dichromate as a catalyst is disclosed in Applied Catalysis, 62 (1990) pp. 119–123. Tetrahedron Letters, 46 (1978), pp 4561–4562 suggests the use of Mn$_2$(SO$_4$)$_3$. It is also suggested in Chemistry Letters, (1985) pp 827–828 that hydrogen peroxide may be used as an oxidant in the presence of Pd(II)-polystyrene sulfonic acid resin.

The method for oxidizing 2-methylnaphthalene to prepare vitamin K$_3$ has a problem; by-products, having no industrial use, such as 6-methyl-1,4-naphthoquinone, as well as 2-methyl-1,4-naphthoquinone, are produced. Thus, a process for isolating 2-methyl-1,4-naphthoquinone from 6-methyl-1,4-naphthoquinone is required. This isolation process is mentioned in Japanese Pat. Laid-Open Publication No. Sho. 60-252445 (1985), Hei. 3-275642 (1991), 4-17172 (1992), EP No. 430,164 (1991), and U.S. Pat. No. 5,329,026 (1994).

Thus, if the conventional oxidation methods of 2-methylnaphthalene are commercialized, many difficult problems will arise in industrial production because the isolation of the by-product after the oxidation is necessary and the disposal of the oxidants used is troublesome. It is also difficult to purify 2-methylnaphthalene from tar. Its synthesis is economically undesirable because the yield is low.

EP No. 636,598 (1995), Japanese Pat. Laid-Open Publication No. Hei. 7-223993 (1995) and U.S. Pat. No. 5,412,124 (1995), suggest an alternative method for preparing 2-methyl-1,4-naphthoquinone without oxidizing 2-methylnaphthalene. According to this method, 1,3-butadiene and 2-methyl-1,4-benzoquinone are subject to a [2+4] Diels-Alder reaction, to produce 2-methyl-4a,5,8,8a-tetrahydro-1,4-naphthoquinone, which is then dehydrogenated to 2-methyl-1,4-naphthoquinone. In addition, there is also a method in which 2-methyl-5,8-dihydro-1,4-naphthalenediol presented in a relatively stable form after the [2+4] Diels-Alder reaction, is electrolytically oxidized in a solution containing a support electrolyte and an organic solvent, to prepare 2-methyl-1,4-naphthoquinone, as disclosed in Japanese Pat. Laid-Open Publication No. Sho. 57-134581 (1982).

These methods utilizing a [2+4] Diels-Alder reaction are very advantageous in that the materials can be relatively easily obtained, there is a minimum generation of by-products, and no particular catalysts are used in the reaction, so that a disposal problem of waste due to oxidants does not occur. However, for the dehydrogenation of the products resulting from the [2+4] Diels-Alder reaction, it is required for them to be isolated and purified, due to their low stability. It is difficult in a commercial scale to use the electrolytic oxidation process.

SUMMARY OF THE INVENTION

The above problems can be solved by a method for preparing 2-methyl-1,4-naphthoquinone according to the present invention. The method for preparing 2-methyl-1,4-naphthoquinone according to the present invention comprises oxidative dehyrogenation of 2-methyl-4a,5,8,8a-tetrahydro-1,4-naphthoquinone, a product of a [2+4] Diels-Alder reaction from 2-methyl-1,4-benzoquinone, and 1,3-butadiene in a single pot, without isolation and purification or pretreatment for the dehydrogenation process. Although 2-methyl-4a,5,8,8a-tetrahydro-1,4-naphthoquinone is a stable compound which can be separated, it is thermodynamically more unstable than 2-methyl-1,4-naphthoquinone. Such a thermodynamical stability of 2-methyl-1,4-naphthoquinone can be utilized in dehydrogenation. That is, the dehydrogenation may be performed in a single pot to shorten the reaction process, without separating 2-methyl-4a,5,8,8a-tetrahydro-1,4-naphthoquinone.

Accordingly, it is an object of the present invention to provide a method for preparing 2-methyl-1,4-naphthoquinone, which comprises dehydrogenating 2-methyl-4a,5,8,8a-tetrahydro-1,4-naphthoquinone, obtained through a [2+4] Diels-Alder reaction of 2-methyl-1,4-benzoquinone with 1,3-butadiene, in the presence of acid catalysts, wherein the [2+4] Diels-Alder reaction and oxidative dehydrogenation are, in sequence, carried out in a single pot, by using dimethylsulfoxide as both a dehydrogenating agent and a solvent for the [2+4] Diels-Alder reaction and using at least one Lewis acid or one Broensted acid as a dehydrogenation catalyst.

DETAILED DESCRIPTION OF THE INVENTION

The present invention relates to a method for preparing 2-methyl-1,4-naphthoquinone, in which 2-methyl-4a,5,8,8a-tetrahydro-1,4-naphthoquinone is formed through a [2+4] Diels-Alder reaction of 2-methyl-1,4-benzoquinone and 1,3-butadiene, and subjected to dehydrogenation without further pretreatment, including isolation and purification, in a single pot.

In order to perform the [2+4] Diels-Alder reaction and the dehydrogenation in a single pot, in accordance with the present invention, it is essential to secure a very mild oxidant that is not involved in the Diels-Alder reaction, but participates only in the dehydrogenation. The present inventors found that dimethylsulfoxide (hereinafter referred to as "DMSO") which has not been known as an oxidant, satisfied this requirement. It is stated in Synthesis (1990) pp. 857–870, that since the oxidation activity of DMSO is very low, its oxidation activity can usually be maintained only by using a strong base or by being activated.

Such oxidative dehydrogenation utilizing strong bases or the unactivated DMSO is not known. But when intermediates are thermodynamically less stable than the starting materials as in the present invention, it was found that DMSO could also be used as a good oxidant or oxidative dehydrogenating agent. In particular, when the intermediates have a carbonyl group, such as 2-methyl-4a, 5,8, 8a-tetrahydro-1, 4-naphthoquinone, it is helpful to the production of 2-methyl-1,4-naphthoquinone which becomes thermodynamically stable, for the carbonyl group to form a complex by at least one Lewis acid or one Broensted acid. From this fact, the acid catalyst is expected to be a good reaction promoter.

In addition, DMSO has a good solubility to acids functioning as a catalyst in the [2+4] Diels-Alder reaction and also dissolves 2-methyl-benzoquinone of which solubility to organic solvents is low, so that the Diels-Alder reaction is promoted. Also the product by oxidative dehydrogenation, 2-methyl-1,4-naphthoquinone, can be obtained in high yield. Therefore, DMSO is used as both a reaction solvent and an oxidant in the present invention.

The acid catalysts include all the catalysts as used in Lewis acids and Broensted acids. For example, $SnCl_4 \cdot nH_2O$, $FeCl_3 \cdot nH_2O$, $AlCl_3$, $BF_3$, p-toluenesulfonic acid, etc. are possible. $SnCl_4 \cdot nH_2O$ is known to be the most effective.

The suitable amount of catalyst to use is in the range of 1 to 70% by weight relative to 2-methyl-1,4-benzoquinone.

The reaction temperature is possible from 100° to 180° C. but a temperature of 130° C. is more suitable for controlling the reaction. If the reaction temperature is too low, the reaction rate slows down and by-products including 2-methyl-4a,5,8,8a-tetrahydro-1,4-naphthoquinone, 2-methyl-5,8-dihydro-1,4-naphthoquinone and 2-methyl-5,8-dihydro-1,4-naphthalenediol are formed.

The present invention takes advantage of a typical homogeneous catalyst system and uses a reactor which can be pressurized in batch. The analytical data of the products are identified by NMR spectra and GC-MSD. Quantitative analytical data under the following conditions using gas chromatography are identified and component ratios calculated in terms of area ratios are used:

Capillary column: ULTRA 1 (Crosslinked Methyl Silicone Gum) 50 m×0.22 mm×0.33 μm Carrier: nitrogen Head pressure: 18 psig Oven: 150° C. (2 min) to 280° C., beta=20° C./min Injection Temp.: 280° C.

Detector & Temp.: FID (280° C.)

Split ratio: 50:1

Makeup gas flowrate: 38 ml

A better understanding of the present invention may be obtained in light of the following examples, which are set forth to illustrate, but are not to be construed to limit the present invention.

EXAMPLE I

In a 100 ml three-neck flask, which could be distilled under reduced pressure and equipped with a cooler and stirrer, 1 g (8.3 mmol) of 2-methyl-1,4-benzoquinone was charged and dissolved in 10 ml of DMSO. To the solution, 1,3-butadiene was added, in the presence of 1.9 mmol of an acid catalyst, as indicated in Table 1 below. This mixture reacted at 130° C. The resulting reactant was dissolved in chloroform and washed twice with water. The chloroform solution was identified and analyzed by the use of NMR spectra and gas chromatography. The results are given as shown in Table 1 below. Good yields were obtained when using $SnCl_4 \cdot 5H_2O$, $FeCl_3 \cdot 6H_2O$ as a Lewis acid or an organic acid as a Broensted acid.

TABLE 1

Yields of Products according to Catalysts

| Catalyst | Yields of Products (%) | | | | | |
|---|---|---|---|---|---|---|
| | A | B | C | D | E | F |
| $FeCl_3 \cdot 6H_2O$ | 7 | — | — | — | 86 | 7 |
| $ZnCl_2$ | 2 | — | 28 | 32 | 30 | 8 |
| $AlCl_3$ | — | 31 | — | — | 56 | 13 |
| $SnCl_4 \cdot 5H_2O$ | — | — | — | — | 94 | 6 |
| p-Toluenesulfonic Acid | 3 | 33 | — | — | 63 | 1 |

A: 2-methyl-1,4-benzoquinone
B: 2-methyl-1,4-benzenediol
C: 2-methyl-4a,5,8,8a-tetrahydro-1,4-naphthoquinone
D: 2-methyl-5,8-dihydro-1,4-naphthoquinone
E: 2-methyl-1,4-naphthoquinone (vitamin $K_3$)
F: 2-methyl-5,8-dihydro-1,4-naphthalenediol

EXAMPLE II

The procedure of Example I was repeated except for using $SnCl_4 \cdot 5H_2O$ as a catalyst at various amounts. The results are given as shown in Table 2 below. As apparent from Table 2, the catalyst enhances conversion and selectivity.

TABLE 2

Yields of Products according to Change in Catalyst Amount

| Catalyst Amount | Yields of Products (%) | | | | | |
|---|---|---|---|---|---|---|
| | A | B | C | D | E | F |
| 0.67 g (1.9 mmol) | — | — | — | — | 94 | 6 |
| 0.29 g (0.8 mmol) | — | — | — | — | 72 | 28 |
| 0.03 g (0.08 mmol) | — | — | — | — | 68 | 32 |
| 0 g | — | 24 | — | — | 37 | 39 |

EXAMPLE III

The reaction was performed in the manner similar to Example II, except that 0.67 g (1.9 mmol) of $SnCl_4 \cdot 5H_2O$ was used as a catalyst and the temperature was changed in the DMSO solvent. The results are given as shown in Table 3 below.

TABLE 3

Yields of Products according to Change in Reaction Temp.

| Reaction Temp. | Yields of Products (%) | | | | | |
|---|---|---|---|---|---|---|
| | A | B | C | D | E | F |
| 50° C. | 60 | — | 11 | 10 | 12 | 7 |
| 80° C. | 3 | — | 9 | 40 | 35 | 13 |
| 130° C. | — | — | — | — | 94 | 6 |
| 160° C. | — | — | — | — | 100 | — |

EXAMPLE IV

The reaction was performed in the manner similar to Example II, except for using DMSO/isopropanol mixtures as indicated in Table 4 below, in order to show the influence of the DMSO solvent. The results are given as shown in Table 4 below. As apparent from Table 4, in the case of using isopropanol alone, more of the starting material was converted into 2-methyl-1,4-benzenediol and undesirable 2-methyl-5,8-dihydro-1,4-naphthalene. As the ratio of DMSO increased, a larger amount of 2-methyl-1,4-naphthoquinone was obtained.

TABLE 4

Yields of Products according to Solvents

| Isopropanol/ DMSO | Yields of Products (%) | | | | | |
|---|---|---|---|---|---|---|
| | A | B | C | D | E | F |
| 100/0 | 1 | 31 | — | 5 | 21 | 42 |
| 80/20 | 47 | — | 23 | 20 | 6 | 4 |
| 50/50 | 1 | — | — | 20 | 58 | 21 |
| 0/100 | — | — | — | — | 94 | 6 |

EXAMPLE V

The reaction was performed in the manner similar to Example IV, except for using xylene instead of isopropanol.

The results are given as shown in Table 5 below. As in Example IV, in the case of using xylene only, the reaction did not proceed well. As the ratio of DMSO increased, the desired reaction proceeded well.

TABLE 5

Yields of Products according to Solvents

| Xylene/ DMSO | Yields of Products (%) | | | | | |
|---|---|---|---|---|---|---|
| | A | B | C | D | E | F |
| 100/0 | — | — | — | — | 22 | 16 (62*) |
| 80/20 | 3 | — | 17 | 54 | 20 | 6 |
| 50/50 | — | — | — | 10 | 56 | 34 |
| 0/100 | — | — | — | — | 94 | 6 |

*yields of unidentified products

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for preparing 2-methyl-1,4-naphthoquinone through a [2+4] Diels-Alder reaction of 2-methyl-1,4-benzoquinone with 1,3-butadiene to obtain 2-methyl-4a,5,8,8a-tetrahydro-1,4-naphthoquinone and a dehydrogenation of the obtained 2-methyl-4a,5,8,8a-tetra-hydro-1,4-naphthoquinone in the presence of a dehydrogenating catalyst, the dehydrogenating catalyst selected from the group consisting of a Lewis acid and a Broensted acid, the method comprising the step of:

carrying out simultaneously the [2+4] Diels-Alder reaction and a dehydrogenation in a single pot by using dimethylsulfoxide as a dehydrogenating agent and as a solvent for the [2+4] Diels-Alder reaction.

2. The method in accordance with claim 1, wherein at least one Lewis acid is selected from the group consisting of $SnCl_4 \cdot nH_2O$, $FeCl_3 \cdot nH_2O$, $AlCl_3$ and $BF_3$ and said Broensted acid is p-toluenesulfonic acid.

3. The method in accordance with claim 1, wherein said dehydrogenation catalyst is used in an amount of 1 to 70% by weight relative to 2-methyl-1,4-benzoquinone.

4. The method in accordance with claim 1, wherein said [2+4] Diels-Alder reaction and said dehydrogenation are carried out at a temperature ranging from 100° to 150° C.

5. The method in accordance with claim 1, wherein said reaction solvent is a mixture of dimethylsulfoxide and an organic solvent.

* * * * *